(12) United States Patent
Chen et al.

(10) Patent No.: US 9,931,120 B2
(45) Date of Patent: Apr. 3, 2018

(54) STAPLE CHAMBER ASSEMBLY AND LINEAR SURGICAL STITCHING DEVICE USING SAID STAPLE CHAMBER ASSEMBLY

(75) Inventors: Wangdong Chen, Jiangsu (CN); Yongwang Pei, Jiangsu (CN); Jing Zhou, Jiangsu (CN)

(73) Assignee: TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 860 days.

(21) Appl. No.: 13/993,070

(22) PCT Filed: Dec. 5, 2011

(86) PCT No.: PCT/CN2011/083483
§ 371 (c)(1),
(2), (4) Date: Aug. 22, 2013

(87) PCT Pub. No.: WO2012/075918
PCT Pub. Date: Jun. 14, 2012

(65) Prior Publication Data
US 2013/0327808 A1    Dec. 12, 2013

(30) Foreign Application Priority Data
Dec. 10, 2010 (CN) .......................... 2010 1 0581554

(51) Int. Cl.
*A61B 17/072* (2006.01)
*A61B 90/00* (2016.01)

(52) U.S. Cl.
CPC ................... *A61B 17/07207* (2013.01); *A61B 2017/07285* (2013.01); *A61B 2090/08021* (2016.02)

(58) Field of Classification Search
CPC .......................... A61B 17/07207; F16B 7/105
(Continued)

(56) References Cited

U.S. PATENT DOCUMENTS 3,980,409 A * 9/1976 Turner ..................... B25G 1/04
                                                    248/188.5
4,079,978 A * 3/1978 McMullin ............... F16B 7/105
                                                      15/3.51
(Continued)

FOREIGN PATENT DOCUMENTS

CN       201171690 Y     12/2008
CN       101449995 A      6/2009
(Continued)

*Primary Examiner* — Thanh Truong
*Assistant Examiner* — Patrick Fry
(74) *Attorney, Agent, or Firm* — Seed IP Law Group LLP

(57) ABSTRACT

A linear surgical stapler includes an upper staple cartridge receiving half-section, a lower staple cartridge receiving half-section and a staple cartridge assembly. The staple cartridge assembly includes a cutting groove in which a reciprocating movement cutter is mounted. The cutter includes a bottom surface and a knife blade located at a far end of the cutter. The staple cartridge assembly includes a restricting member mounted therein and an elastic stopper. The elastic stopper abuts against the restricting member when the staple cartridge assembly is in an initial state. The restricting member breaks away from the staple cartridge assembly when the staple cartridge assembly is in a firing complete state, thereby preventing the cutter from sliding towards the far end of the staple cartridge. As a result, misfiring throughout the whole operation of the linear surgical stapler is prevented.

5 Claims, 3 Drawing Sheets

(58) Field of Classification Search
USPC .................. 227/175.2, 175.4; 403/109.3
See application file for complete search history.

(56) References Cited

U.S. PATENT DOCUMENTS

| | | | |
|---|---|---|---|
| 5,129,570 A | 7/1992 | Schulze et al. | |
| 5,156,315 A | 10/1992 | Green et al. | |
| 5,413,267 A * | 5/1995 | Solyntjes | A61B 17/072 227/175.4 |
| 5,632,432 A * | 5/1997 | Schulze | A61B 17/07207 227/176.1 |
| 5,693,042 A | 12/1997 | Boiarski et al. | |
| 5,865,361 A | 2/1999 | Milliman et al. | |
| 6,988,649 B2 * | 1/2006 | Shelton, IV | A61B 17/07207 227/175.2 |
| 7,044,352 B2 * | 5/2006 | Shelton, IV | A61B 17/07207 227/175.1 |
| 7,055,730 B2 | 6/2006 | Ehrenfels et al. | |
| 7,140,528 B2 * | 11/2006 | Shelton, IV | A61B 17/07207 227/175.2 |
| 7,300,444 B1 | 11/2007 | Nielsen et al. | |
| 7,407,076 B2 * | 8/2008 | Racenet | A61B 17/072 227/175.1 |
| 7,641,092 B2 * | 1/2010 | Kruszynski | A61B 17/072 227/175.2 |
| 7,644,848 B2 | 1/2010 | Swayze et al. | |
| 8,328,064 B2 * | 12/2012 | Racenet | A61B 17/072 227/175.2 |
| 8,905,977 B2 | 12/2014 | Shelton et al. | |
| 2007/0102475 A1 * | 5/2007 | Ortiz | A61B 17/07207 227/175.2 |
| 2010/0065604 A1 * | 3/2010 | Weng | A61B 17/07207 227/175.2 |

FOREIGN PATENT DOCUMENTS

| | | |
|---|---|---|
| CN | 101849851 A | 10/2010 |
| CN | 101991452 A | 3/2011 |
| CN | 201930014 U | 8/2011 |
| CN | 101856251 B | 10/2011 |
| EP | 2 018 826 A2 | 1/2009 |
| WO | 03/094745 A1 | 11/2003 |

* cited by examiner

STAPLE CHAMBER ASSEMBLY AND LINEAR SURGICAL STITCHING DEVICE USING SAID STAPLE CHAMBER ASSEMBLY

This application claims the benefit of priority to Chinese Patent Application No. 201010581554.7 titled "A KIND OF LINEAR SURGICAL STAPLER", filed with the Chinese State Intellectual Property Office on Dec. 10, 2010, the entire disclosure of which is incorporated herein by reference.

FIELD OF THE INVENTION

The present invention relates to a staple cartridge assembly and a linear surgical stapler having such staple cartridge assembly, which belongs to the technical fields of medical devices.

BACKGROUND OF THE INVENTION

Surgical stitching instruments have been widely used in surgical operations for stitching up wounds, and stitching up and cutting interior tissues. U.S. Pat. No. 5,129,570 discloses a typical surgical stitching instrument which is provided with double functions of stitching and cutting. That is to say, the surgical stitching instrument is capable of stitching up wounds and simultaneously cutting spilth tissues. Such surgical stitching instruments usually include a pair of top and bottom forceps, a closing handle for closing the top and bottom forceps, an anvil and a staple cartridge respectively mounted on opposite far ends of the top and bottom forceps, a staple-pushing rod, a staple-pushing piece and a cutter all moveably mounted in the staple cartridge, and a push button for moveably pushing the staple-pushing piece and the cutter. The staple cartridge includes inside stitch nails which are pushed by the staple-pushing piece to move towards the anvil. The tissues between the staple cartridge and the anvil are cut off by the cutter.

Error firing action means that after the instrument has been fired, it refires without any nails in the reloading unit. The consequence of such error firing action will extrude the nails which have already well closed and will cause over-deformation of the nails. As a result, the wound closure cannot be good enough, and serious medical malpractices and sequelae sometimes occur.

In order to avoid this kind of phenomenon, the conventional surgical stitching instruments usually have safely mechanisms for error firing protection.

U.S. Pat. No. 5,129,570 discloses such a safety mechanism which includes a middle safety block having a cutter channel and a staple-pushing rod channel, and an elastic piece mounted below the cutter. When the instrument is at an open position, which means the top and bottom forceps are not closed, the cutter are upsprung by the elastic piece so that the cutter cannot pass the cutter channel. When the instrument is loaded with the staple cartridge, a transverse lever which is pivotally mounted on top of the staple cartridge presses against a top portion of the cutter. The cutter overcomes the elasticity of the elastic piece and recovers to a position where the cutter can pass through the cutter channel. As a result, under this condition, the instrument can be used in firing. When the instrument is completely fired, the cutter is pulled back to the original position. Under this condition, the transverse lever has been pivoted to a position where the transverse lever cannot press the top portion of the cutter anymore. The cutter is upsprung again by the elastic piece so that the cutter cannot pass the cutter channel and thereby preventing error firing.

U.S. Pat. No. 7,055,730 discloses another safety mechanism which includes a protection cover mounted on the cutter. The protection cover is connected to the staple cartridge through a pin and the protection cover is rotatable with respect to the pin under the function of a torsional spring. The protection cover is mateable with and connected to the cutter before firing of the instrument for not only protecting the blade, but also keeping horizon for closing the instrument. When the instrument is completely fired, the cutter returns back to the original position. Under this condition, the protection cover breaks away from the cutter, once the instrument is opened, the protection cover overturns immediately under the function of the torsional spring. The protection cover is ultimately and vertically located between the anvil and the staple cartridge which results in the instrument unclosed, thereby avoiding the error firing possibility of the instrument. However, in fact, such safely mechanism cannot absolutely avoid empty firing of the instrument between the time after the firing of the instrument is complete and before the instrument is opened. Therefore, the conventional second error firing protection cannot continue the entire process between the time when the firing of the instrument is complete and before a new staple cartridge is installed. Thus, certain operation risk still exists.

BRIEF SUMMARY OF THE INVENTION

An object of the present application is to provide a staple cartridge assembly with simple structure for preventing error firing, and a linear surgical stapler having such staple cartridge assembly.

In order to solve the above technical problems, it is provided according to an illustrated embodiment of the present application a staple cartridge assembly including a cutting groove in which a reciprocating movement cutter is mounted. The cutter includes a bottom surface and a knife blade located at a far end of the cutter. The staple cartridge assembly includes a restricting member mounted therein and an elastic stopper for mating with the restricting member. The restricting member and the elastic stopper define a first position and a second position. The elastic stopper abuts against the restricting member when the elastic stopper is located at the first position. The restricting member (4) breaks away from the staple cartridge assembly when the elastic stopper is located at the second position.

Preferably, the elastic stopper includes a moveable button and a spring resisting against a bottom portion of the moveable button.

Preferably, the staple cartridge assembly includes a through hole in which the moveable button and the spring are accommodated. An axis of the through hole is perpendicular to and in communication with a central line of the cutting groove. A top portion of the moveable button is extendable beyond the through hole under the function of the spring.

Preferably, the staple cartridge assembly includes a cushion block, the cushion block being fixed to the staple cartridge assembly, and another end of the spring resisting against a top surface of the cushion block.

Preferably, the through hole includes a step and the moveable button includes an embossment under condition that an external diameter of the embossment is larger than an internal diameter of the step.

Preferably, the top portion of the moveable button is of a wedge configuration.

Preferably, the elastic stopper includes a rotatable block and a torsion spring acting on the rotatable block.

Preferably, the rotatable block includes a limiting surface for restricting movement of a cutter-pushing rod when the staple cartridge assembly is in a firing state.

Preferably, a minimum distance between the limiting surface and a rotating axis of the rotatable block is larger than a perpendicular distance between the bottom surface and the rotating axis of the rotatable block.

Preferably, the elastic stopper is structured as an elastic metal piece, one end of which is fixedly connected to a bottom portion of the staple cartridge assembly.

In order to solve the above technical problems, it is also provided according to an illustrated embodiment of the present application a linear surgical stapler comprising an upper staple cartridge receiving half-section, a lower staple cartridge receiving half-section and a staple cartridge assembly for supporting the lower staple cartridge receiving half-section. The staple cartridge assembly includes a cutting groove in which a reciprocating movement cutter is mounted. The cutter includes a bottom surface and a knife blade located at a far end of the cutter. The staple cartridge assembly comprises a restricting member mounted therein and an elastic stopper for mating with the restricting member. The restricting member and the elastic stopper define a first position and a second position. The elastic stopper abuts against the restricting member when the elastic stopper is located at the first position. The restricting member (4) breaks away from the staple cartridge assembly when the elastic stopper is located at the second position.

Preferably, the elastic stopper includes a moveable button and a spring resisting against a bottom portion of the moveable button.

Preferably, the staple cartridge assembly includes a through hole in which the moveable button and the spring are accommodated. An axis of the through hole is perpendicular to and in communication with a central line of the cutting groove. A top portion of the moveable button is extendable beyond the through hole under the function of the spring.

Preferably, the staple cartridge assembly includes a cushion block, the cushion block being fixed to the staple cartridge assembly, and another end of the spring resisting against a top surface of the cushion block.

Preferably, the through hole includes a step and the moveable button includes an embossment under condition that an external diameter of the embossment is larger than an internal diameter of the step.

Preferably, the top portion of the moveable button is of a wedge configuration.

Preferably, the elastic stopper includes a rotatable block and a torsion spring acting on the rotatable block.

Preferably, the rotatable block includes a limiting surface for restricting movement of a cutter-pushing rod when the staple cartridge assembly is in a firing state.

Preferably, a minimum distance between the limiting surface and a rotating axis of the rotatable block is larger than a perpendicular distance between the bottom surface and the rotating axis of the rotatable block.

Preferably, the elastic stopper is structured as an elastic metal piece, one end of which is fixedly connected to a bottom portion of the staple cartridge assembly.

In order to solve the above technical problems, it is also provided according to an illustrated embodiment of the present application a staple cartridge assembly comprising a cutting groove in which a reciprocating movement cutter is mounted. The cutter includes a bottom surface and a knife blade located at a far end of the cutter. The staple cartridge assembly comprises a restricting member mounted therein, an elastic stopper and a receiving cavity located at a far-end bottom section of the staple cartridge assembly for receiving the restricting member. The staple cartridge assembly defines an initial state and a firing state. The restricting member is located on top of the elastic stopper and prevents a top end of the elastic stopper from protruding beyond the bottom surface when the staple cartridge assembly is in the initial state. The restricting member is remained in the receiving cavity in order that the top end of the elastic stopper engages with the cutter to thereby preventing reciprocating movement of the cutter when the firing state of the staple cartridge assembly is completed.

Preferably, the elastic stopper comprises a moveable button and a spring resisting against a bottom portion of the moveable button. The restricting member is located on top of the moveable button when the restricting member is in the initial state.

Preferably, the staple cartridge assembly further includes a through hole in which the moveable button and the spring are accommodated. An axis of the through hole is perpendicular to and in communication with a central line of the cutting groove. A top portion of the moveable button is extendable beyond the through hole under the function of the spring.

Preferably, the staple cartridge assembly further includes a cushion block, the cushion block being fixed to the staple cartridge assembly, and another end of the spring resisting against a top surface of the cushion block.

Preferably, the through hole comprises a step and the moveable button comprises an embossment under condition that an external diameter of the embossment is larger than an internal diameter of the step.

Preferably, the top portion of the moveable button is of a wedge configuration.

Preferably, the elastic stopper comprises a rotatable block and a torsion spring acting on the rotatable block. The restricting member is located on top of the rotatable block when the restricting member is in the initial state.

Preferably, the rotatable block comprises a limiting surface for restricting movement of a cutter-pushing rod when the staple cartridge assembly is in the firing state.

Preferably, a minimum distance between the limiting surface and a rotating axis of the rotatable block is larger than a perpendicular distance between the bottom surface and the rotating axis of the rotatable block.

Preferably, the elastic stopper is structured as an elastic metal piece under condition that one end of the elastic metal piece is fixedly connected to a bottom portion of the staple cartridge assembly, and the other end of the elastic metal piece engages against a bottom portion of the restricting member when the staple cartridge assembly is in the initial state and restricts movement of a cutter-pushing rod when the staple cartridge assembly is in the firing state.

In order to solve the above technical problems, it is also provided according to an illustrated embodiment of the present application a linear surgical stapler comprising an upper staple cartridge receiving half-section, a lower staple cartridge receiving half-section and a staple cartridge assembly for supporting the lower staple cartridge receiving half-section. The staple cartridge assembly comprises a cutting groove in which a reciprocating movement cutter is mounted. The cutter includes a bottom surface and a knife blade located at a far end of the cutter. The staple cartridge assembly comprises a restricting member mounted therein, an elastic stopper and a receiving cavity located at a far-end bottom section of the staple cartridge assembly for receiving the restricting member. The staple cartridge assembly defines an initial state and a firing state. The restricting member is located on top of the elastic stopper and prevents a top end of the elastic stopper from protruding beyond the bottom surface when the staple cartridge assembly is in the initial state. The restricting member is remained in the receiving cavity in order that the top end of the elastic stopper engages with the cutter to thereby preventing reciprocating movement of the cutter when the firing state of the staple cartridge assembly is completed.

Preferably, the elastic stopper comprises a moveable button and a spring resisting against a bottom portion of the moveable button. The restricting member is located on top of the moveable button when the restricting member is in the initial state.

Preferably, the staple cartridge assembly further includes a through hole in which the moveable button and the spring are accommodated. An axis of the through hole is perpendicular to and in communication with a central line of the cutting groove. A top portion of the moveable button is extendable beyond the through hole under the function of the spring.

Preferably, the staple cartridge assembly further includes a cushion block, the cushion block being fixed to the staple cartridge assembly, and another end of the spring resisting against a top surface of the cushion block.

Preferably, the through hole comprises a step and the moveable button comprises an embossment under condition that an external diameter of the embossment is larger than an internal diameter of the step.

Preferably, the top portion of the moveable button is of a wedge configuration.

Preferably, the elastic stopper comprises a rotatable block and a torsion spring acting on the rotatable block. The restricting member is located on top of the rotatable block when the restricting member is in the initial state.

Preferably, the rotatable block comprises a limiting surface for restricting movement of a cutter-pushing rod when the staple cartridge assembly is in the firing state.

Preferably, a minimum distance between the limiting surface and a rotating axis of the rotatable block is larger than a perpendicular distance between the bottom surface and the rotating axis of the rotatable block.

Preferably, the elastic stopper is structured as an elastic metal piece under condition that one end of the elastic metal piece is fixedly connected to a bottom portion of the staple cartridge assembly, and the other end of the elastic metal piece engages against a bottom portion of the restricting member when the staple cartridge assembly is in the initial state and restricts movement of a cutter-pushing rod when the staple cartridge assembly is in the firing state.

Compared to the prior arts, the present application provides the advantage of simple structure, and prevents misfiring throughout the whole operation from the completion of a firing to the exchange of a new staple cartridge, thereby eliminating the possibility of misfiring after a first firing and providing more safely.

DETAILED DESCRIPTION OF THE PREFERRED EMBODIMENTS

Figure 1:
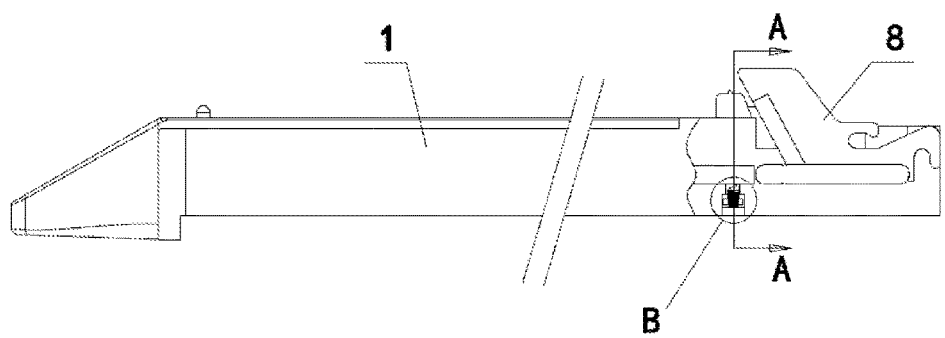
FIG. 1 is a structural schematic view of a staple cartridge assembly in accordance with a first illustrated embodiment of the present application.
Figure 2:
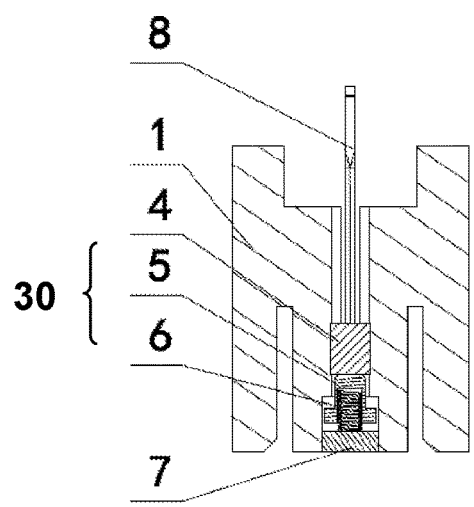
FIG. 2 is a cross-sectional view taken along line A-A of FIG. 1.

The present application discloses a linear surgical stapler, especially a staple cartridge assembly. As shown in FIGS. 1 to 4, the same as prior arts, the present application according to a first embodiment includes a staple cartridge 1 and a knife base 2 fixed with each other. The staple cartridge 1 includes a cutting groove in which a cutter 8 is mounted. The cutter 8 is movable back and forth along the axis of the cutting groove. The cutter 8 includes a bottom surface 10 and a knife blade 11. Certainly, the staple cartridge 1 therein further includes a positioning hole, a staple-pushing piece and a nail disposed inside the positioning hole etc. Since such structures are irrelated to the present application, detailed description thereabout is omitted herein.

First Embodiment

The staple cartridge 1 includes a through hole 3 located adjacent to a near-end bottom side of the staple cartridge 1. The through hole 3 is in communication with the cutting groove. According to the present application, a front-to-back direction means a left-to-right direction of the drawings, and a top-to-bottom direction means a top-to-bottom direction of the drawings. In a preferred embodiment, the through hole 3 is associated therein a moveable button 5 which is capable of reciprocating movement along an axis of the through hole. The bottom side of the moveable button 5 is provided with a spring 6. One end of the spring 6 abuts against the moveable button 5 so that the moveable button 5 always suffers a pushing force which directly tends towards the bottom surface 10. The bottom side of the spring 6 is provided with a cushion block 7 which is securely fixed to the bottom face of the staple cartridge 1. The other end of the spring 6 resists against a top surface of the cushion block 7. In this wise, the moveable button 5 is always driven by the spring 6 to move towards the cutter 8.

Figure 3:
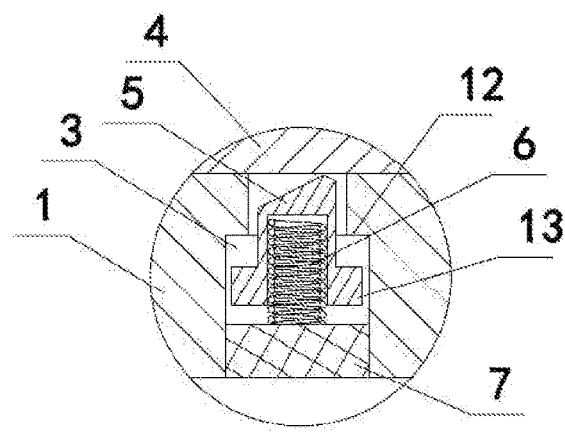
FIG. 3 is an enlarged view of portion B of FIG. 1.
Figure 4:
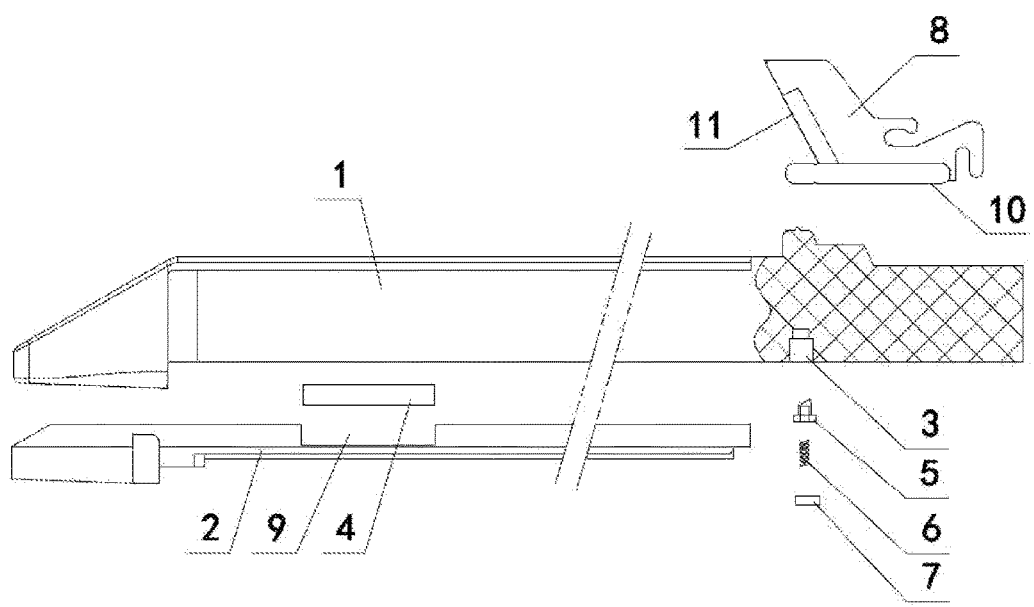
FIG. 4 is an exploded schematic view of the staple cartridge assembly in accordance with the first illustrated embodiment of the present application.

Certainly, the cushion block 7 can be omitted and let the other end of the spring 6 directly resisting on the knife base 2. Referring to FIG. 3, the through hole 3 includes a step 12 and the moveable button 5 includes an embossment 13 for mating with the step 12. An external diameter of the embossment 13 is larger than an internal diameter of the step 12 as a result that even if the force of the spring 6 is always applied to the moveable button 5, the moveable button 5 can be prevented from withdrawing the through hole 3. Furthermore, referring to the drawings, a top portion of the moveable button 5 is of a wedge configuration. The top portion of the moveable button 5 is extendable beyond the through hole 3 under the function of the spring 6. In the current embodiment, the moveable button 5 and the spring 6 together form an elastic stopper 30.

The staple cartridge assembly according to the present application defines two states including an initial state and a firing complete state. When the staple cartridge assembly is in the initial state, a sliding block 4 is provided on top of the through hole 3 and forward the cutter 8. The sliding block 4 is a kind of restricting member. The sliding block 4 is located on top of the moveable button 5 and generates a relative acting force applied to the moveable button 5. The sliding block 4 can be of any shapes and the illustrated rectangular shape is only for demonstration. In the present application, as long as the sliding block 4 capable of sliding from a near-end of the staple cartridge to a far-end of the staple cartridge is okay. The knife base 2 includes a recess 9 at the far-end thereof. Both the width and the height are larger than or equal to those of the sliding block 4. The maximum distance between the recess 9 and the through hole 3 is smaller than or equal to a movable distance of the cutter 8. As a result, it is insure that when the sliding block 4 slides from the near-end to the far-end of the staple cartridge, it can be dropped out into the recess 9. In order to make the sliding block 4 falls into the recess 9 much easier, front and rear sides of the sliding block can be designed with slope surfaces. Alternatively, the receiving cavity for receiving the sliding block can be arranged at the farthest bottom portion of the staple cartridge or the farthest portion of the cutter, thereby the receiving cavity can be a vacant area rather than the recess. The vacant area is located at the farthest staple cartridge and cannot be reached by the cutter.

The following working process of the preferred embodiment will be described in simple.

When the staple cartridge assembly is in the initial state, the moveable button 5, the spring 6 and the cushion block 7 are assembled in the through hole 3 of the staple cartridge in turn. The sliding block 4 is sandwiched between the moveable button 5 and the bottom surface 10 with the sliding block 4 pressing against the moveable button 5. When the staple cartridge is in the firing process, the sliding block 4 is pushed to move forwardly by the cutter 8. During sliding, the sliding block 4 will fall into the predetermined recess 9 to prevent the sliding block 4 from returning back to the initial position. In such process, the moveable button 5 always resists against the bottom surface 10 of the cutter 8. When the staple cartridge assembly is in the firing complete state, the cutter 8 is pulled back to the initial position where the moveable button 5 breaks away from the sliding block 4. Under this condition, without the oppression of the slider block 4, the moveable button 5 is upsprung by the spring 6 and is fixed to the far-end of the knife blade 11. As a result, the cutter 8 is restricted by the moveable button 5 to prevent the cutter 8 from moving forwardly. The instrument of the present application can be prevented from second error refiring and thereby realizing the purpose of the present application.

Second Embodiment

Figure 5:
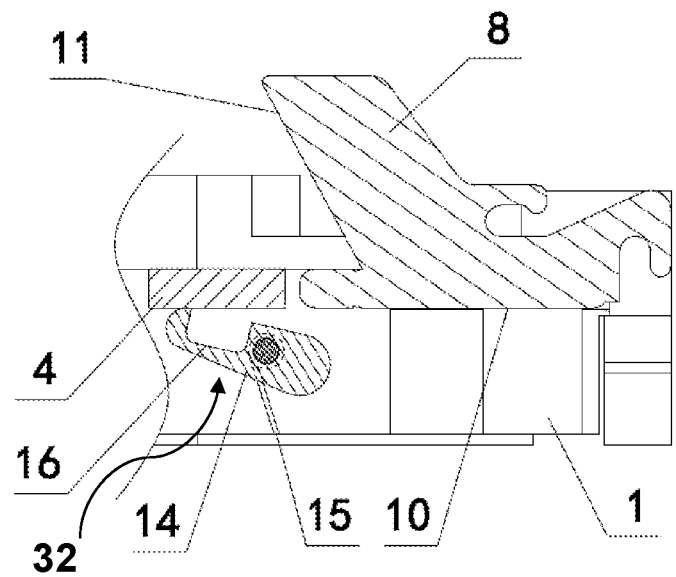
FIG. 5 is a structural schematic view of a staple cartridge assembly in accordance with a second illustrated embodiment of the present application when the staple cartridge assembly is in an initial state.
Figure 6:
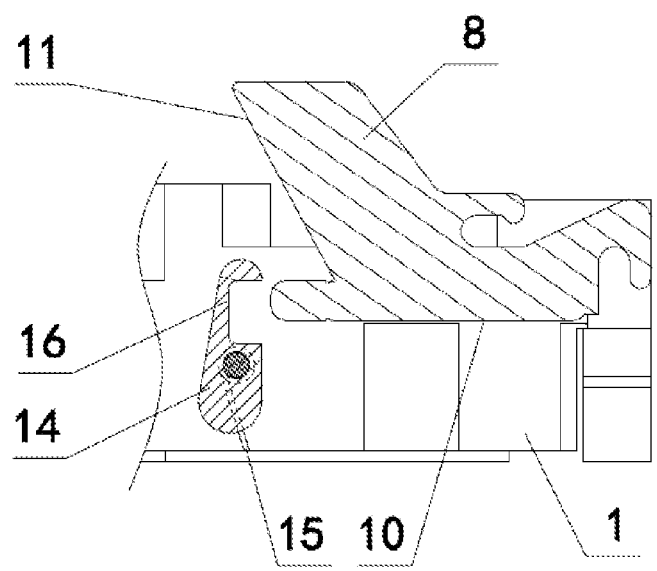
FIG. 6 is a structural schematic view of the staple cartridge assembly in accordance with the second illustrated embodiment of the present application when the staple cartridge assembly is in a firing state.

Referring to FIGS. 5 and 6, according to the current embodiment, the elastic stopper 32 includes a rotatable block 14 pivotally mounted in the staple cartridge and a torsion spring 15 acting on the rotatable block 14. The torsion spring 15 always applies an acting force for driving the rotatable block 14 rotating clockwise. The rotatable block 14 includes a limiting surface 16 for restricting movement of a cutter-pushing rod when the staple cartridge assembly is in the firing state. The sliding block 4 is located on top of the rotatable block 14 in the initial state.

When the staple cartridge assembly is in the initial state as shown in FIG. 5, the sliding block 4 presses against the rotatable block 14. When the staple cartridge is in the firing process, the sliding block 4 is pushed to move forwardly by the cutter 8. During sliding, the sliding block 4 will fall into the predetermined recess 9 to prevent the sliding block 4 from returning back to the initial position. In such process, the moveable button 5 always resists against the bottom surface 10 of the cutter 8. When the staple cartridge assembly is in the firing complete state, as shown in FIG. 6, the cutter 8 is pulled back to the initial position where the moveable button 5 breaks away from the sliding block 4. Under this condition, without the oppression of the slider block 4, the rotatable block 14 rotates clockwise by the torsion spring 15. In this embodiment, a minimum distance between the limiting surface 16 and a rotating axis of the rotatable block 14 is larger than a perpendicular distance between the bottom surface 10 and the rotating axis of the rotatable block 14. As a result, it is insure that when the rotatable block 14 rotates to the state as shown in FIG. 6, the limiting surface 16 can be fixed to the far-end of the knife blade 11. Thereby, the cutter 8 is restricted by the rotatable block 14 to prevent the cutter 8 from moving forwardly. The instrument of the present application can be prevented from second error refiring and thereby realizing the purpose of the present application.

The far-end of the present application is an end far from an operator and the near-end is an end near the operator. The present application may have multiple embodiments, for example, the elastic stopper includes an elastic metal piece with one end fixedly connected to a bottom portion of the staple cartridge assembly, and the other end abutting against the bottom portion of the sliding block 4 when the staple cartridge assembly is in the initial state. When the staple cartridge assembly is in the firing state, since the sliding block is received in the recess 9, the other end of the elastic metal piece protrudes a certain distance. The elastic metal piece can be fixed to the far-end of the knife blade 11. Thereby, the cutter 8 is restricted by the rotatable block 14 to restrict movement of the cutter-pushing rod. It should be noted that, those skilled in the art may make many improvements and modifications to the present application without departing from the principle of the present application, and these improvements and modifications also fall into the protection scope of the claims of the present application.

What is claimed is:
1. A staple cartridge assembly, comprising:
   a reciprocating movement cutter which is moveable along a longitudinal direction, the cutter comprising a bottom surface and a knife blade located at a far end of the cutter;
   a sliding block which is slideable in the longitudinal direction; and
   a stopper for mating with the sliding block, the staple cartridge assembly having a receiving space positioned at a far end of the staple cartridge assembly and an initial state and a firing state, wherein,
   in operation from the initial state to the firing state, the stopper is consistently pressed by the sliding block so that the cutter can move forward in the longitudinal direction together with the sliding block;
   after completing the firing state, the sliding block is left in the receiving space and the stopper extends beyond the bottom surface of the cutter in order that the cutter is prevented from further moving forward along the longitudinal direction, wherein the receiving space comprises a recess and the sliding block falls into the recess during the operation from the initial state to the firing state;

the stopper comprises a moveable button and a spring resisting against a bottom portion of the moveable button;

the staple cartridge assembly further comprises a through hole in which the moveable button and the spring are accommodated, an axis of the through hole being perpendicular to the longitudinal direction, a top portion of the moveable button being extendable beyond the through hole under the function of the spring;

the recess has a width and a height that are larger than or equal to those of the sliding block; and a maximum distance between the recess and the through hole is smaller than or equal to a movable distance of the cutter.

2. The staple cartridge assembly as claimed in claim 1, further comprising a cushion block, the cushion block being fixed to the staple cartridge assembly, one end of the spring resisting against the moveable button, and the other end of the spring resisting against a top surface of the cushion block.

3. The staple cartridge assembly as claimed in claim 2, wherein the through hole comprises a step and the moveable button comprises an embossment under condition that an external diameter of the embossment is larger than an internal diameter of the step.

4. The staple cartridge assembly as claimed in claim 3, wherein the top portion of the moveable button is of a wedge configuration.

5. A linear surgical stapler, comprising:
   a staple cartridge receiving section; and
   a staple cartridge assembly, including:
      a reciprocating movement cutter which is moveable along a longitudinal direction, the cutter comprising a bottom surface and a knife blade located at a far end of the cutter;
      a sliding block which is slideable in the longitudinal direction; and
      a stopper for mating with the sliding block, the staple cartridge assembly having a receiving space positioned at a far end of the staple cartridge assembly and an initial state and a firing state, wherein, in operation from the initial state to the firing state, the stopper is consistently pressed by the sliding block so that the cutter can move forward in the longitudinal direction together with the sliding block;

after completing the firing state, the sliding block is left in the receiving space and the stopper extends beyond the bottom surface of the cutter in order that the cutter is prevented from further moving forward along the longitudinal direction, wherein the receiving space comprises a recess and the sliding block falls into the recess during the operation from the initial state to the firing state;

the stopper comprises a moveable button and a spring, resisting against a bottom portion of the moveable button;

the staple cartridge assembly comprises a through hole in which the moveable button and the spring are accommodated, an axis of the through hole being perpendicular to the longitudinal direction, a top portion of the moveable button being extendable beyond the through hole under the function of the spring;

the recess has a width and a height that are larger than or equal to those of the sliding block; and a maximum distance between the recess and the through hole is smaller than or equal to a movable distance of the cutter.

* * * * *